United States Patent
Bocko et al.

(10) Patent No.: US 9,037,221 B2
(45) Date of Patent: May 19, 2015

(54) NON-CONTACT ELECTROCARDIOGRAM SYSTEM

(71) Applicant: University of Rochester, Rochester, NY (US)

(72) Inventors: Mark F. Bocko, Caledonia, NY (US); Guo Chen Peng, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 51 days.

(21) Appl. No.: 13/742,546

(22) Filed: Jan. 16, 2013

(65) Prior Publication Data
US 2014/0200469 A1 Jul. 17, 2014

(51) Int. Cl.
| | |
|---|---|
| *A61B 5/0402* | (2006.01) |
| *A61B 5/04* | (2006.01) |
| *A61B 5/0245* | (2006.01) |
| *A61B 5/00* | (2006.01) |
| *A61B 5/0408* | (2006.01) |

(52) U.S. Cl.
CPC ........... *A61B 5/04017* (2013.01); *A61B 5/0006* (2013.01); *A61B 5/0245* (2013.01); *A61B 5/04085* (2013.01); *A61B 5/725* (2013.01); *A61B 5/7405* (2013.01); *A61B 5/746* (2013.01); *A61B 5/7214* (2013.01); *A61B 2562/0214* (2013.01)

(58) Field of Classification Search
CPC ........... A61B 5/04012–5/04018; A61B 5/0402
USPC .................................................. 600/509, 513
See application file for complete search history.

(56) References Cited

U.S. PATENT DOCUMENTS

| | | | |
|---|---|---|---|
| 4,926,868 A * | 5/1990 | Larsen ........................ | 600/508 |
| 2008/0000304 A1* | 1/2008 | Nagle et al. .................. | 600/535 |
| 2009/0138059 A1* | 5/2009 | Ouwerkerk ...................... | 607/5 |

* cited by examiner

*Primary Examiner* — Joseph Dietrich
(74) *Attorney, Agent, or Firm* — William Greener; David Nocilly; Bond, Schoeneck & King, PLLC (57) ABSTRACT

A non-contact electrocardiogram (ECG) sensor having an ECG electrode and guard electrode coupled to an electronic circuit that actively gain-corrects the electrocardiogram signal based on fringe capacitance signal and filters the gain-corrected signal based on a static charge reference signal. The compensation system first makes a gain correction for the preamplifier to address ECG electrode-to-subject motion and then removes any additive static common mode interference from motion-induced static charge generation.

14 Claims, 13 Drawing Sheets

NON-CONTACT ELECTROCARDIOGRAM SYSTEM

BACKGROUND OF THE INVENTION

1. Field of the Invention

The present invention relates to electrocardiogram monitoring and, more particularly, to non-contacting electrodes that may work through a subject's clothing.

2. Description of the Related Art

Sensors and systems for electrocardiogram (ECG) measurements have been developed and refined for many years. The front-end of all ECG systems consists of the sensor electrodes and preamplifiers. Traditional adhesive sensor electrodes provide a stable, low impedance signal source that allow for the low noise measurement of ECG signals but the wires and adhesives employed are unsuitable for long term use; even common 24-48 hour Holter monitoring sessions are a considerable inconvenience and discomfort to the user so longer term personal health monitoring with traditional adhesive electrodes would be unworkable.

Non-contact biosensors for cardiac monitoring are of great interest for a number of long-term health sensing applications ranging from exercise and fitness monitoring to management of chronic health conditions, and may be built into emergency medical equipment, examining tables, beds or other furniture. However, the presence of motion-related artifacts and common mode interference remains a challenging problem for several reasons. First, interference from AC power mains may corrupt electrocardiograph signals due to low common mode rejection ratio (CMRR) of the sensor system. Interfering signals can be reduced by employing a driven right leg (DRL) connection, active shielding and guarding of cables, and by employing a notch filter at the output.

Second, triboelectrically generated static charge caused by rubbing between the electrodes and the subject's clothing is another problem as is common mode electrostatic charge on the subject. In addition to reducing movement at the electrode-subject interface, other ways to reduce this effect include the choice of materials that minimize static electric charge generation and providing a static charge discharge path at the electrode subject interface.

Third, the modulation of the bioelectric potential signals from motion-related source impedance changes presents a problem. The signal gain may be a function of the source capacitance and any stray capacitance at the preamplifier input, which can lead to baseline wandering and gain distortion. This effect can be minimized by employing a voltage mode preamplifier, as opposed to a charge-mode preamplifier, however the noise of the voltage mode preamplifier then becomes a consideration.

Finally, electronic noise interferes with the operation of non-contact biosensors. The preamplifier immediately following the ECG electrode is the major contributor to the overall electronic noise level, and may be addressed by employing careful preamplifier design.

Changes in source capacitance due to the relative motion of the electrodes and the subject leads to modulation of both the signals of interest as well as the above mentioned sources of interference and noise, which in turn may generate interference within the signal band of interest. This effect may be large enough in practical scenarios to completely obscure the ECG signal.

In addition, there has been some work on ECG data correction using adaptive filtering. In this work accelerometers were employed as ancillary sensors to monitor motion and then a digital correction was applied to the ECG signal by an adaptive filtering algorithm. However, the accelerometers were not attached at the precise point of the ECG electrodes and thus the accelerometer output was not strongly correlated to changes in the ECG electrode capacitance, thereby limiting the effectiveness of this method.

Traditionally, non-contact sensors are built with high impedance voltage follower amplifiers but, due to the small signal source capacitance, the input capacitance of the amplifier must be kept extremely small or otherwise neutralized, which degrades the noise performance. To cope with small bioelectric signals, a charge amplifier design may be used because the gain is independent of the input capacitance of the preamplifier. The disadvantage of a charge amplifier design is that its gain depends on the source capacitance, which may be modulated by the relative motion of the subject and the ECG electrodes. Other advantages of the charge amplifier configuration are that shielding is straightforward, and the low-frequency cutoff is independent of the source capacitance. In clinical ECG applications the driven right leg (DRL) technique is commonly used to achieve high common mode rejection ratio (CMRR); this technique can be employed with either voltage or current mode preamplifiers. However, the DRL method is not feasible in an ambulatory setting. Accordingly, there is a need for an alternative design of a non-contact ECG sensor that can lead to a more accurate correction method.

BRIEF SUMMARY OF THE INVENTION

An embodiment of the invention provides a monolithic, non-contact ECG sensor system comprising electrodes and a charge amplifier based ECG sensor system integrated onto a single circuit board. In a non-limiting, exemplary aspect, four closely spaced electrodes were used to measure the ECG signal. This arrangement gives a robust and convenient heart rate monitor, however the interpretation of short base-line ECG measurements in more sophisticated morphological analysis of ECG signals must be done with care. In order to correct the gain dependence of the charge amplifier on the source capacitance, an aspect of the embodied invention employs a method in which the subject to electrode gap is continuously monitored by a secondary sensing circuit. This secondary circuit uses the same electrodes that are employed to measure the ECG signal. The electrodes are monitored simultaneously by the ECG readout and the secondary displacement readout. The outputs can be employed to correct the gain of the primary ECG monitoring circuit and any additive interference signals. The compensation system first makes a gain correction for the preamplifier due to ECG electrode to subject motion and then the additive static common mode interference from motion induced static charge generation is removed. The self-contained system according to the embodied invention may advantageously be placed in proximity to the subject or worn in clothing.

BRIEF DESCRIPTION OF THE DRAWINGS

Embodiments and aspects of the invention will be more fully understood and appreciated by reading the following Detailed Description in conjunction with the accompanying drawings, in which.

DETAILED DESCRIPTION OF EXEMPLARY, NON-LIMITING EMBODIMENTS OF THE INVENTION

Figure 1:
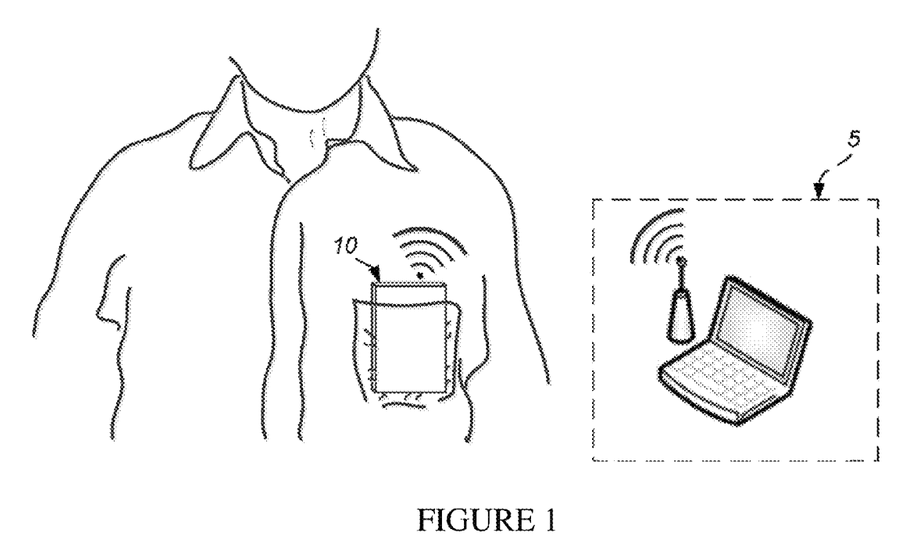
FIG. 1 is a perspective view of the electrocardiogram data acquisition device applied to a patient in combination with a wireless transceiver base, according to an exemplary aspect of the invention.
Figure 2A:
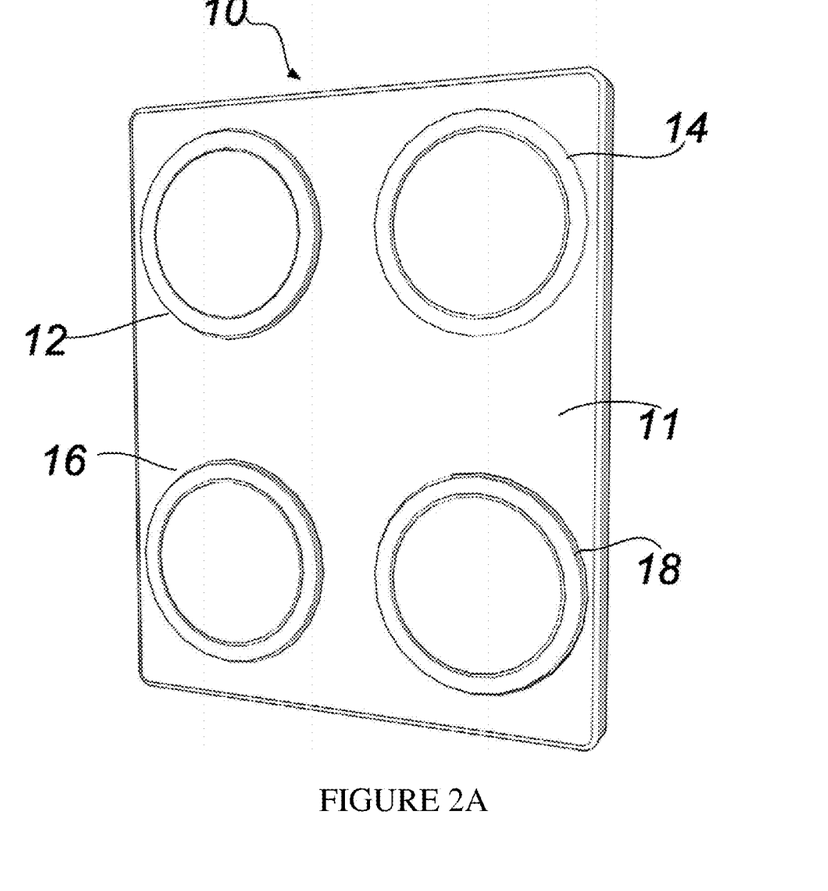
FIGS. 2A and 2B are perspective views of the front side and the back side of a sensor according to an exemplary aspect the invention.
Figure 2B:
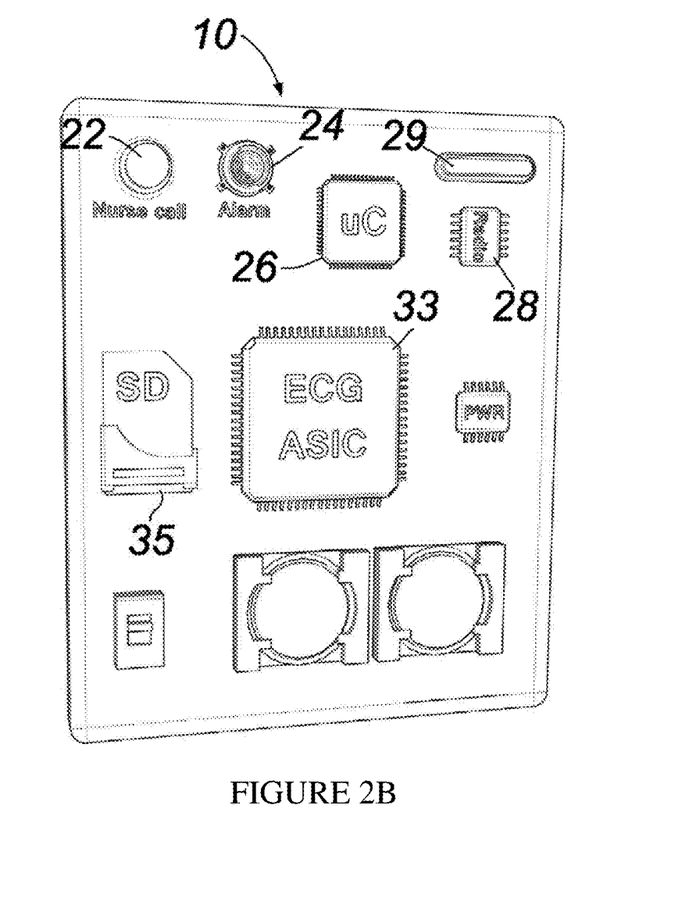

Referring now to the drawings, wherein like reference numerals refer to like parts throughout, there is seen in FIG. 1 a compact, credit card-sized sensor system 10 for measuring cardiac signals. The measured data can be wirelessly transmitted from system 10 to a user base station 5 for recording and analysis. System 10 includes four equally spaced and equal area cardiac sensors 12, 14, 16, and 18 as shown in FIG. 2A. The plane 11 is electrically shielded and grounded. System 10 further includes a front-end analog processing unit 33 labeled as ECG ASIC (Application Specific Integrated Circuit), a microcontroller 26, memory unit 35, radio communication circuit 28, antenna 29, power conditioning and power source unit and, optionally, an alarm (nurse call) button 22, and alarm speaker 24, as detailed in FIG. 2B.

Figure 3:
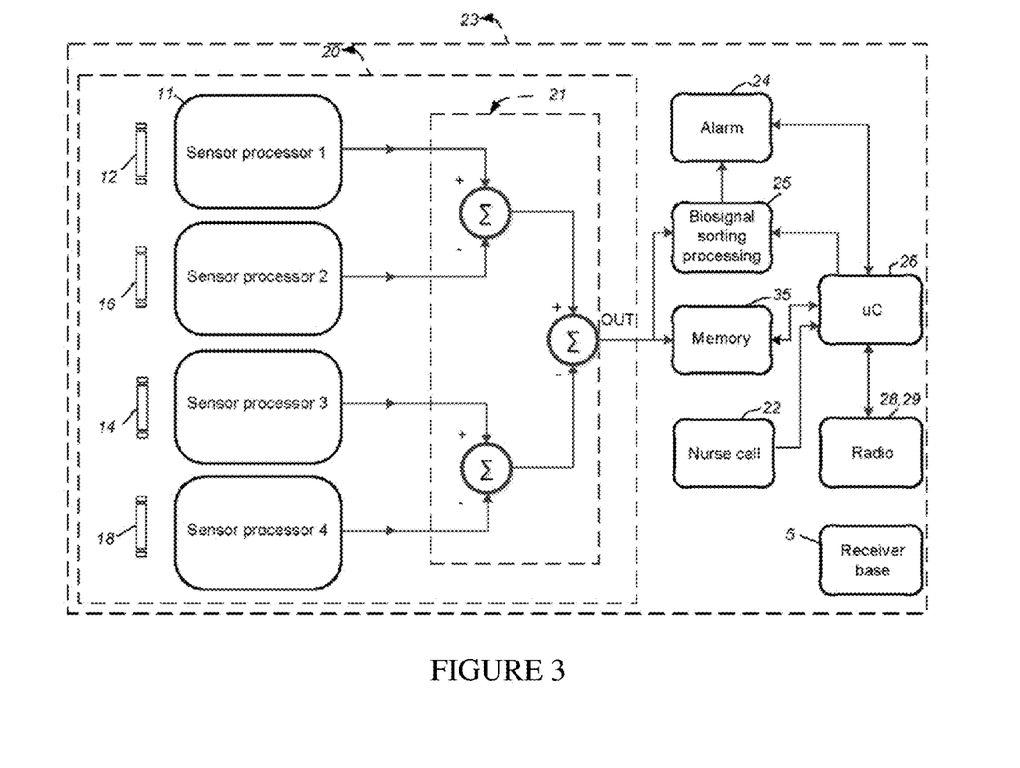
FIG. 3 is a block diagram illustrating an electric non-contact ECG sensor according to an exemplary aspect of the invention.

An exemplary signal processing system 23 for system 10 is illustrated in FIG. 3. A sensor processor 20 is responsible for processing the signals from each of four capacitive sensors 11 that are associated with cardiac sensors 12, 14, 16, and 18. The OUT of processor 20 is calculated by a differential scheme 21 and then stored in memory 35. The data may then be wirelessly transmitted to base station 5 through a radio transceiver 28 coupled to an antenna 29. The OUT of processor 20 may also be processed by a bio-signal sorting module 25, which is programmed to detect heart arrhythmias. If an abnormality is detected, an alarm signal would be sent from alarm 24 to user base station 5 and/or sounded locally by alarm 24. Optionally, a nurse or emergency call 22 may send an alarm signal to base station 5.

Figure 4:
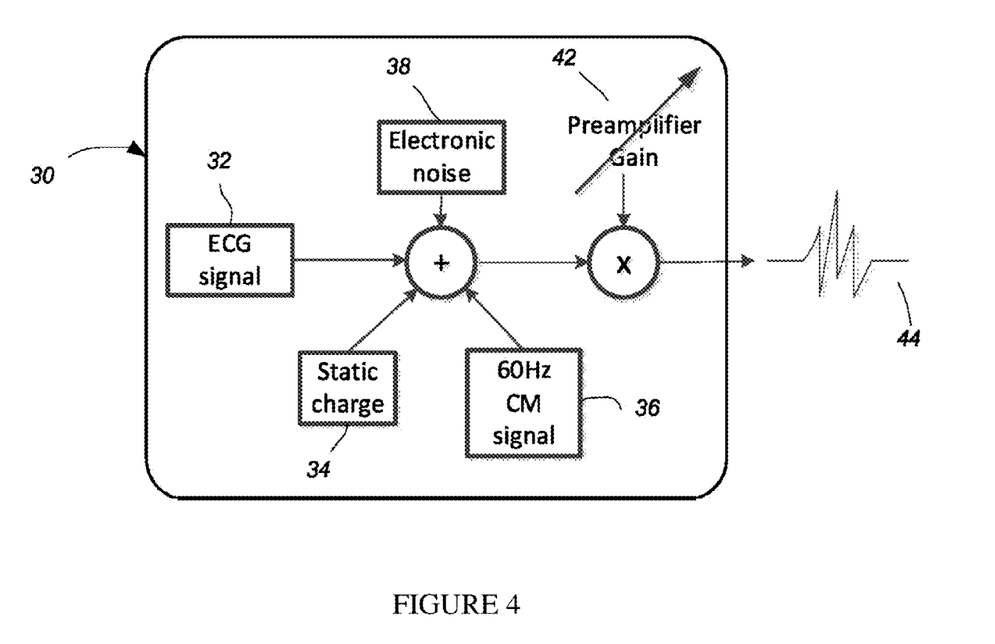
FIG. 4 is a block diagram illustrating noise and interference for non-contact ECG sensing.
Figure 5:
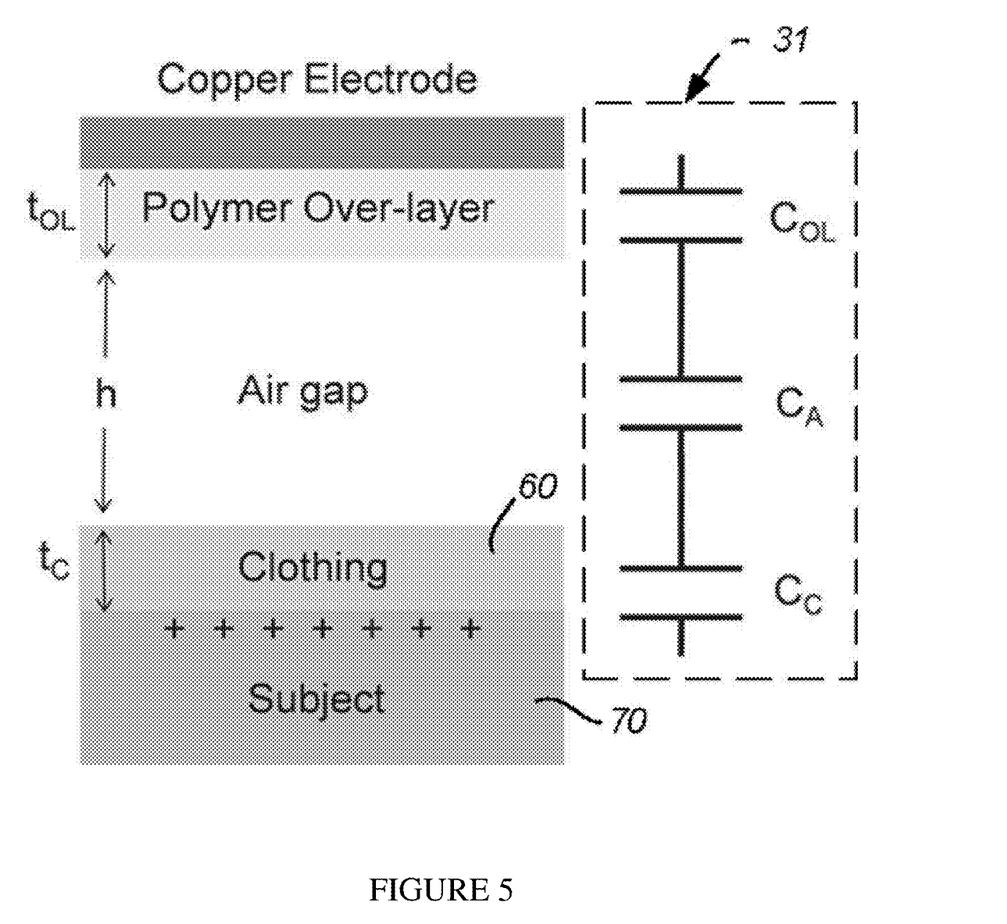
FIG. 5 is a schematic of the total source capacitance for non-contact ECG electrode interfacing with a subject through clothing.

There is seen in FIG. 4 an example model of a motion artifact signal 30 according to the present invention. As the source capacitance 31, seen in FIG. 5, changes, the resulting output from the preamplifier is distorted because the amplifier transfer function is dependent upon the source capacitance. The source signal includes the original ECG signal 32 and common mode signals 34 and 36, which may be created from static charge generation, AC noise, or any potential difference between the subject virtual ground and the reference of the measurement system. The distorted output 44 is a combination of the pure ECG signal 32 with additive noise sources 34, 36 and 38 multiplied by preamplifier gain 42. According to this relationship, monitoring the source capacitance and estimating the additive noise sources can allow for the recovery of the original ECG signal.

Figure 6A:
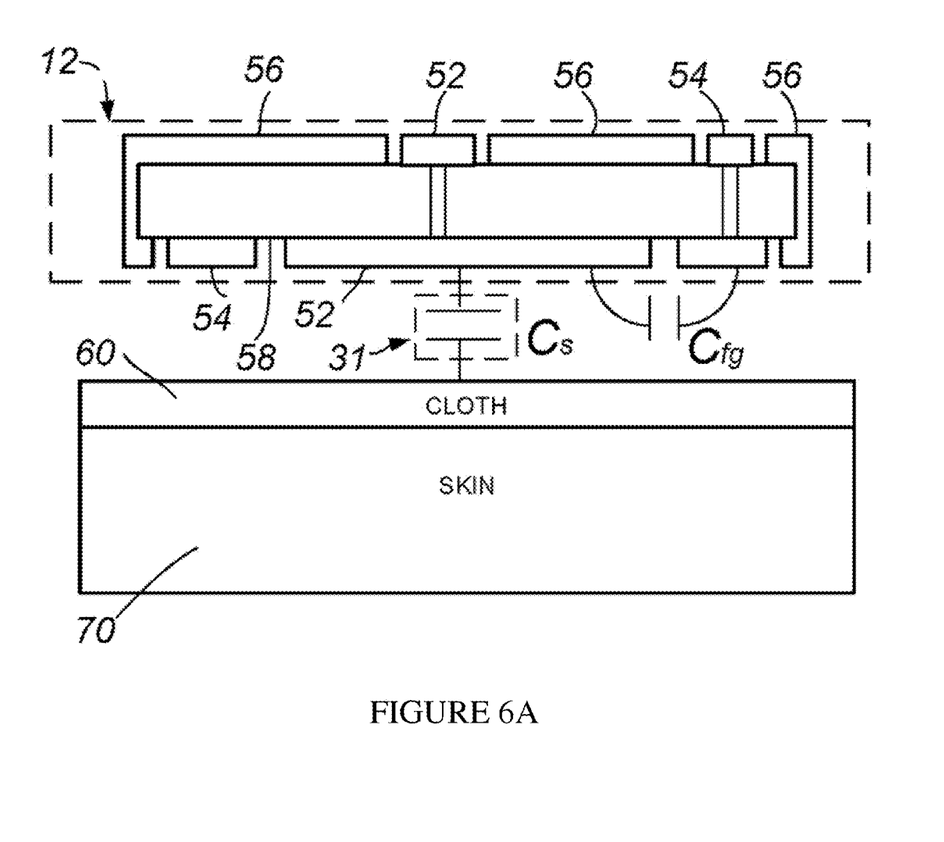
FIG. 6A is a cross-sectional view of a sensor according to an exemplary aspect of the invention.
Figure 6B:
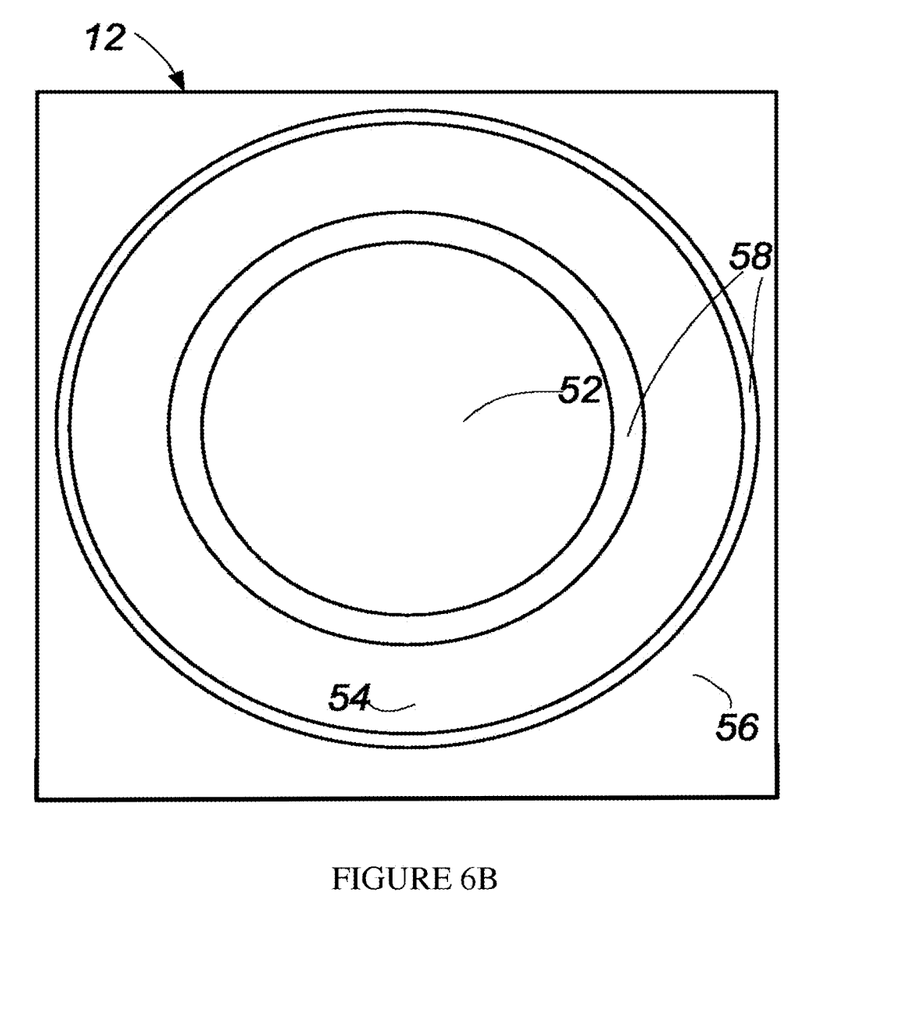
FIG. 6B is a front view of a sensor according to an exemplary aspect of the invention.

There is seen in FIG. 6 an ECG sensor 12 having a primary ECG electrode 52, a secondary electrode 54, and an electrical guard plane 56, each of which is separated by insulating material 58. Capacitance 31 from primary ECG electrode 12 to the subject is a function of the gap and electrode area. At the same time, the capacitance ($C_{fg}$) between secondary electrode 54 and ECG electrode 52 is also a function of the sensor-to-subject gap as well as other geometric factors. By monitoring the fringe capacitance, the ECG electrode-to-subject capacitance ($C_s$) 31 may be directly inferred.

Figure 7:
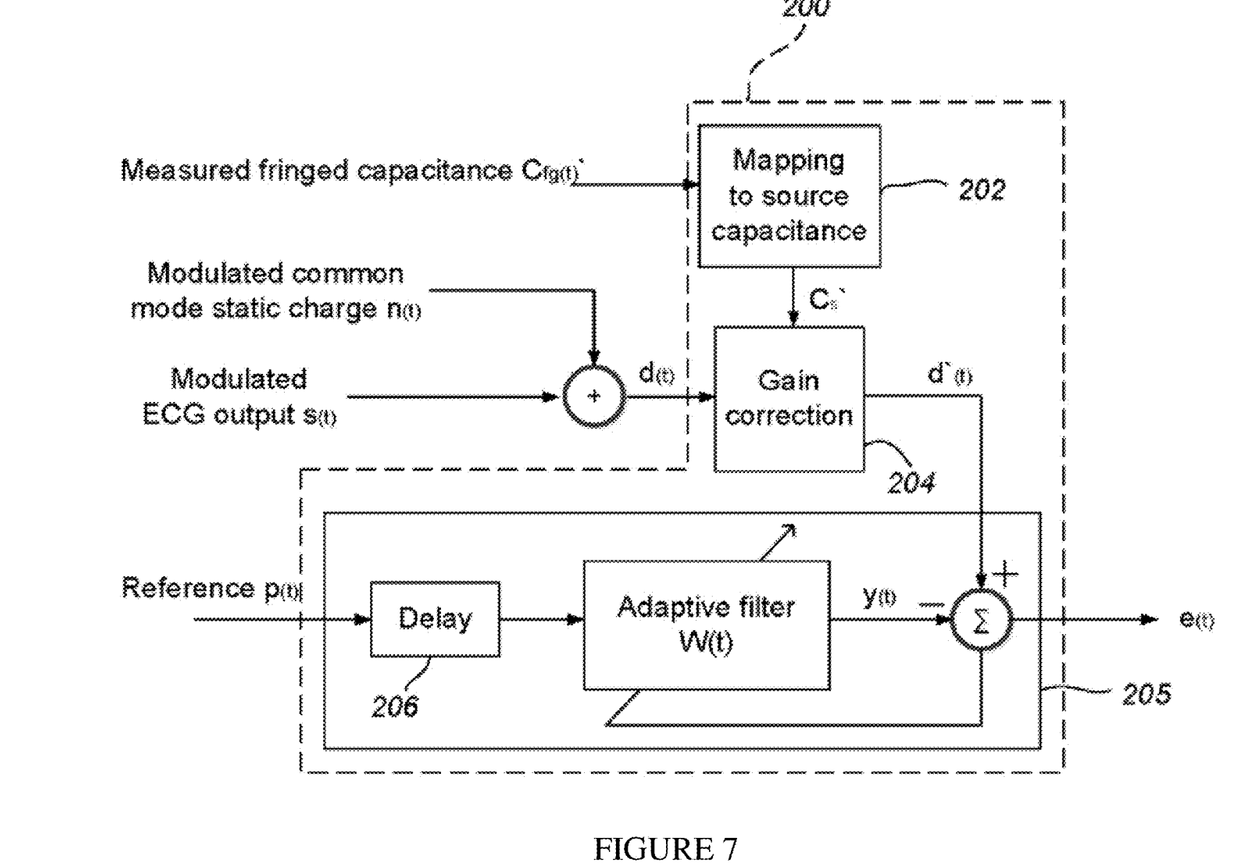
FIG. 7 is a block diagram illustrating a non-contact ECG signal compensation algorithm scheme of a non-contact electrode for the present invention.

As seen in FIG. 4, corrupted signal 44 is made up of two additive parts: the common mode static charge signals 34 and 36, and the ECG signal 32, where both are modulated by changes in the source capacitance. Electronic noise 38 is assumed to be negligible compared to other spurious signal sources, which is generally true in non-contact sensing applications. Therefore, the artifacts can be sorted into additive and modulation types. Using the auxiliary displacement signal enables gain correction of ECG signal 32 with an adaptive filtering module 200. Referring to FIG. 7, adaptive filtering module 200 includes two subsystems 204 and 205 for processing three primary inputs; the measured fringed capacitance ($C_{fg}'$), the distorted ECG signal (d), and the static charge reference signal (p). System 10 first makes the gain correction and then eliminates the additive static common mode interference.

More particularly, the first step in the process of adaptive filtering module 200 is that the measured fringe capacitance ($C_{fg}'$) is converted into an equivalent source capacitance value by a mapping to source capacitance sub-module 202. With the distorted ECG signal 44, source capacitance ($C_s'$) can be used to actively gain-correct the distorted signal 44, which can be expressed as:

$$d' = d*k/C_s'$$

where k is an empirically determined scaling factor. After the gain correction process, the residual signal d' contains only two additive terms: a purely linear scaled ECG signal (s') and a common mode static charge interference (n'). The AC noise 36 can be filtered out by the use of a notch filter or with careful shielding.

Next, subsystem 205 employs an adaptive filtering method to remove the additive noise. The signal (d') consists of a linearly scaled ECG signal (s') and static charge interference (n') 34 as shown in FIG. 4. Therefore, the measured reference (p) should be highly correlated with the common mode static charge (n'). It should be noted that there is a time delay 206 between the acquisition of the two primary inputs due to a time constant difference between the ECG pre-amplifier and the electrostatic meter sensor readout. The goal of subsystem 205 is to minimize system error (e). Subsystem 205 output is defined as:

$$e = d' - y = s' + n' - y$$

where y corresponds to the filtered additive noise. The mean square error can therefore be expressed as:

$$E[e^2] = E[(s' + n' - y)^2]$$

$$E[e^2]=E[(s')^2]+2(E[s'n']-E[s'y])+E[(n'-y)^2] \qquad (1)$$

where E[ ] denotes the expected value of a random variable; it is assumed that the ECG and the modulated interference signals are uncorrelated, and therefore, $$E[e^2]=E[(s'^2]+E[(n'-y)^2] \qquad (2)$$

By equation (2), the task for the adaptive filter is to make $$E[(n'-y)^2]=0$$

in order to estimate (s), so the system error will be minimized. That is:

$$E[e^2]=E[s'^2]$$

Therefore, the interference corrected signal, i.e., the reconstructed ECG signal, is equal to (e). The adaptive filter must be able to minimize (n'−y) by an appropriate iterative algorithm such as the Least-Mean Square (LMS) algorithm due to its computational simplicity compared to other available algorithms. The filter is expressed as, $$W_{t+1} = W_t + \mu e_t p_t \qquad (3)$$

where $$W_t = \begin{bmatrix} w(1)_t \\ w(2)_t \\ \ldots \\ w(k)_t \end{bmatrix},$$

$$p_t = \begin{bmatrix} p_t \\ p_{t-1} \\ \ldots \\ p_{t-k+1} \end{bmatrix}$$

and where $W_t$ is a set of filter weights, (1, 2, ... k) samples at time t, $p_t$ is the reference noise correlated with n' at time t, and μ is empirically determined. $W_t$ is iteratively updated by the best least-squares estimate of each sample based on:

$$e_t = d'_t - y_t.$$

Figure 8:
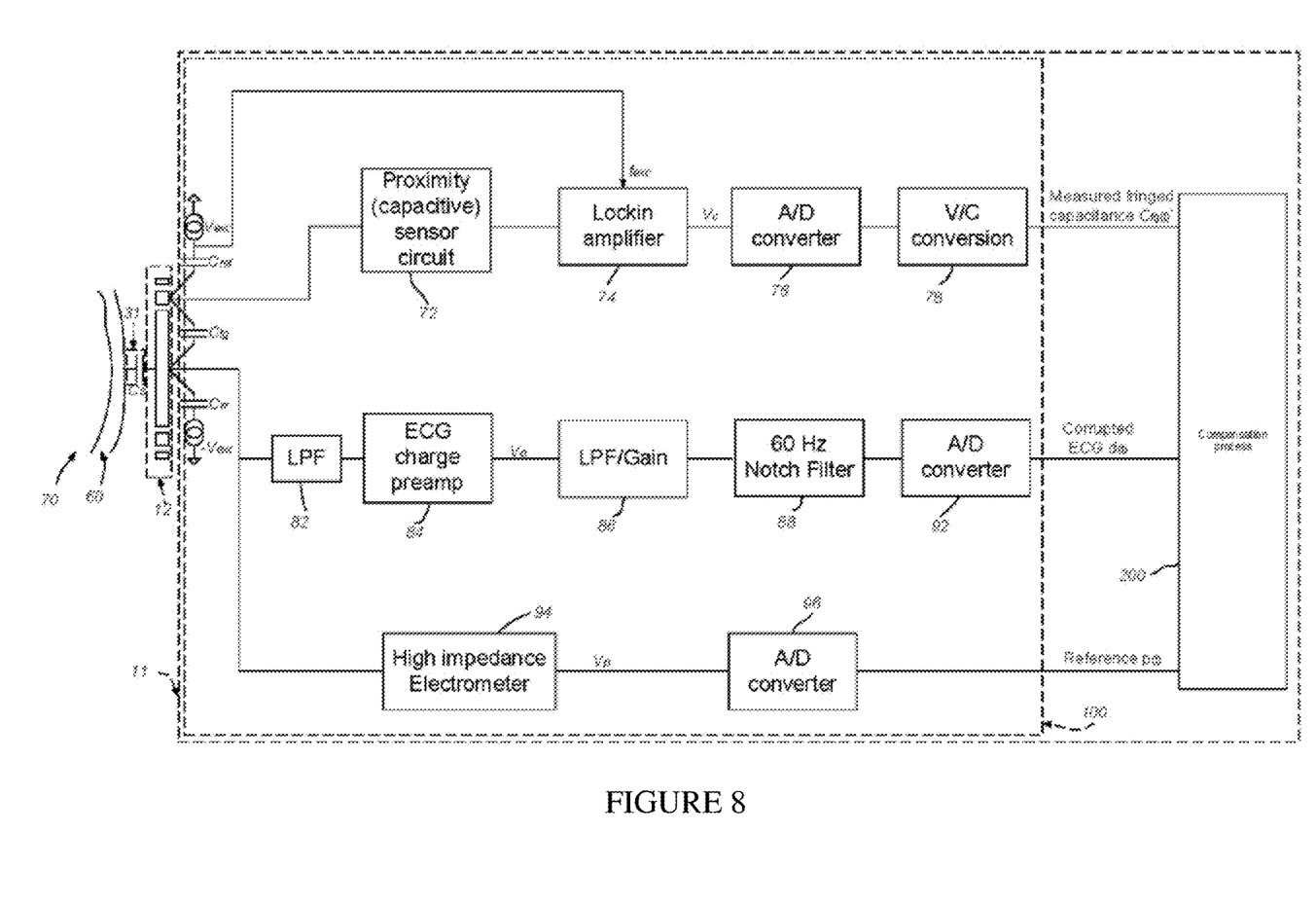
FIG. 8 is a block diagram schematically illustrating an ECG signal compensation scheme of a non-contact electrode for the present invention.

The full readout 100 for the ECG sensor, the proximity sensor, and static charge electrometer is shown in FIG. 8. A patient 70 is capacitively sensed through clothing 60 with sensor 12. The input terminal of the proximity sensor bridge circuit 72 is coupled to secondary electrode 54, while the ECG charge preamplifier 84 is coupled through a lowpass filter 82 to primary ECG electrode 52. The use of a lowpass filter removes the high frequency signals introduced by the proximity sensor 72, as described below. A high impedance electrometer 94 serves as a static charge monitor for the input reference (p).

Figure 9:
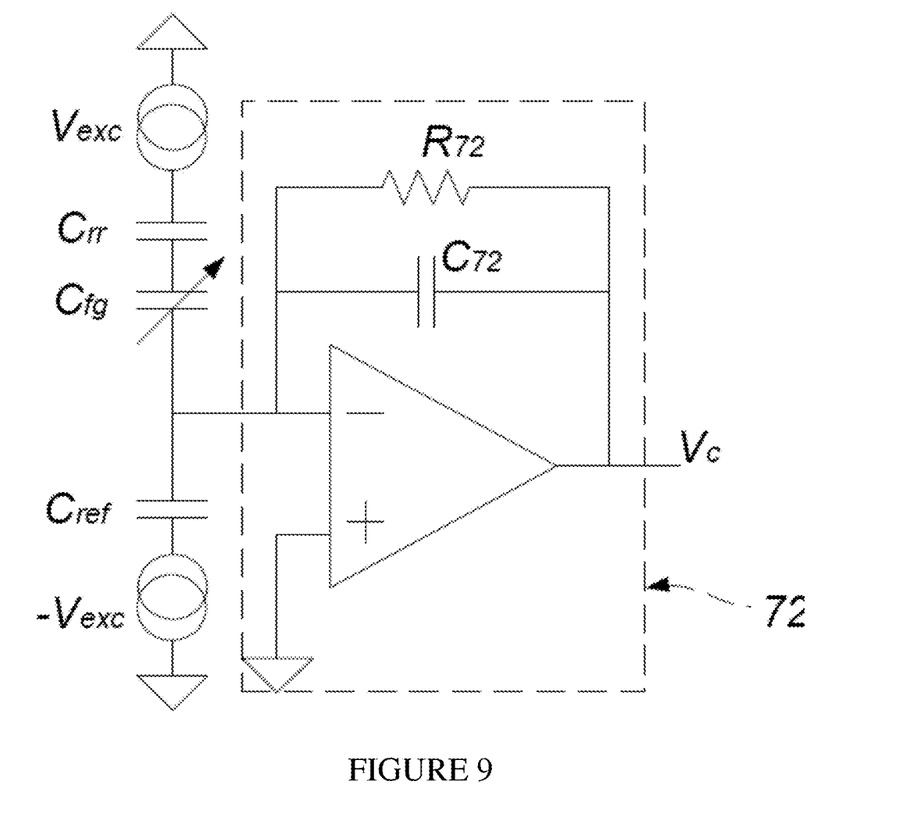
FIG. 9 is a circuit diagram of a proximity sensor used in the embodiment of the invention depicted in FIG. 8.

In an exemplary aspect, the measured fringe capacitance readout employs three capacitors $C_{fg}$, $C_{rr}$, and $C_{ref}$ and a capacitive bridge readout circuit 72, a lock-in amplifier 74, or other suitable phase sensitive detector, an analog-to-digital converter (ADC) 76, and a voltage-to-capacitance converter 78. A detailed circuit diagram of an exemplary bridge circuit 72 is shown in FIG. 9. $C_{ref}$ is a fixed value reference capacitor and $C_{fg}$ is the fringe capacitance to be measured. A high value capacitor $C_{rr}$ serves as a DC block for the excitation signal. $R_{72}$ provides a bias current path and defines a low frequency cutoff. The readout circuit is a capacitive bridge structure with two AC excitation current sources as shown. The lock-in amplifier captures the amplitude response at the excitation frequency. If $C_{ref}$ and $C_{fg}$ are equal, the output of the circuit is zero, otherwise, the output will be proportional to the difference of $C_{ref}$ and $C_{fg}$. The measured fringe capacitance can be expressed as:

$$C'_{fg} = \frac{(C_{rr})(V_{exc}C_{ref} + V_C C_{72})}{V_{exc}(C_{rr} - C_{ref}) - V_C C_{72}} \qquad (5)$$

The low pass filter 82 is used to filter out the excitation signal $V_{exc}$, to prevent ECG amplifier saturation. The amplifier output ($V_o$), which is proportional to $C_s/C_f$ can be further amplified 86 and filtered 88. The digitized output for the system 200 after analog to digital conversion (ADC) 92 is (d).

Figure 10:
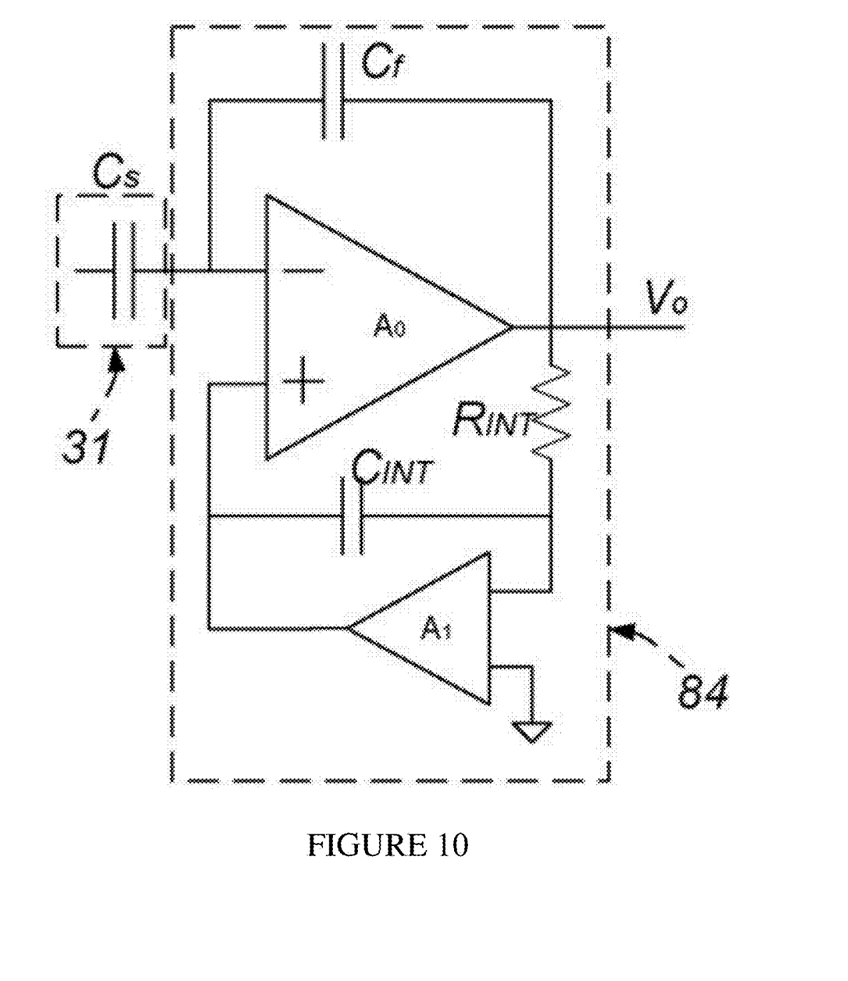
FIG. 10 is a circuit diagram of an ECG preamplifier sensor for use with the embodiment of the invention depicted in FIG. 8.

An example of an ECG charge preamplifier 84 is illustrated in FIG. 10, which shows a charge amplifier with a capacitive transducer ($C_s$) at its input. The charge amplifier consists of a composite amplifier ($A_0$) and a feedback capacitor ($C_f$). There also is a feedback integrator with $R_{INT}$, $C_{INT}$, and an operational amplifier ($A_1$). The gain is determined by the ratio of the signal source capacitance ($C_s$) and the first-stage feedback capacitor ($C_f$). In this case, the ECG signal, other noise sources, and excitation voltage are modulated by the source capacitance ($C_s$).

Figure 11:
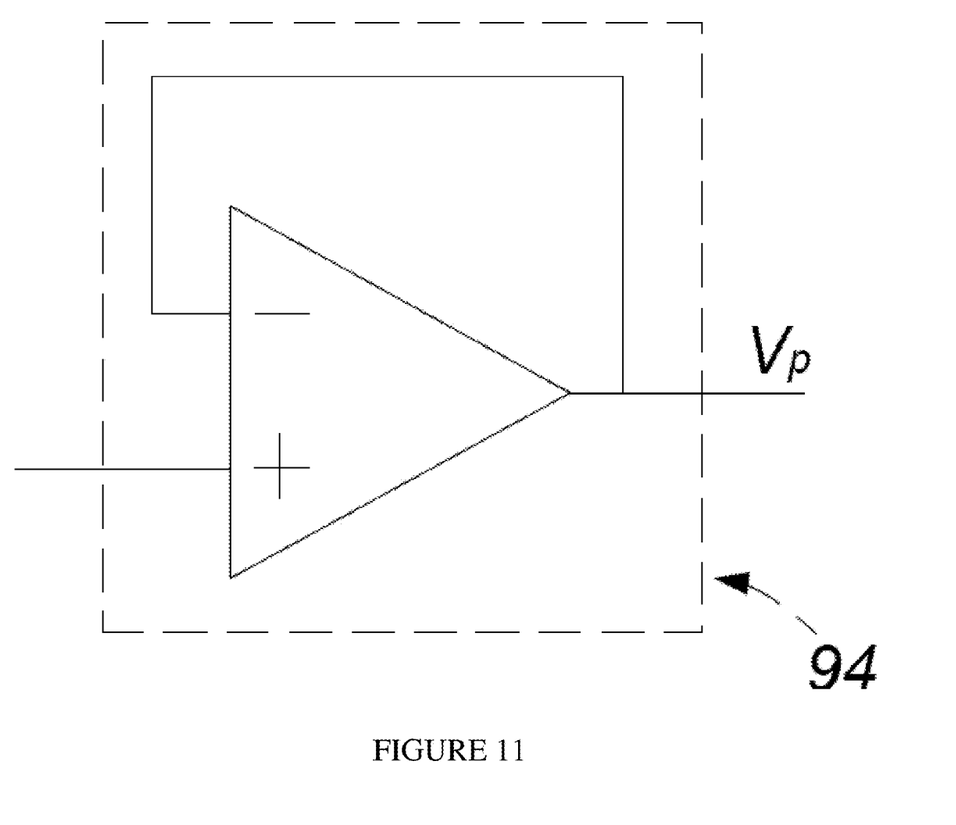
FIG. 11 is a circuit diagram of a static charge electrometer used in particular embodiment of the invention in FIG. 8.

Rubbing between the electrode and the subject's clothing generates a static charge. A third common mode interference correlated source (p) can be acquired by a high impedance electrometer 94, as shown in FIG. 11. The output $V_p$ reveals any voltage fluctuation, which is indicative of the electrode surface charge, and hence may serve as the third input to system 200.

The measured analog data can be digitized in a microprocessor 26, as shown in FIG. 3. The compensation system of adaptive filtering module 200 may be implemented in an on-board microprocessor 26 using algorithm 205. As will be appreciated by those of skill in the art, the various circuits contemplated in the present invention may be provided in analog circuitry, digitally in a microcontroller or microprocessor, or any combination thereof.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A non-contact electrocardiogram sensor, comprising:
    an electrode array comprising at least one sensing electrode for outputting an electrocardiogram signal and at least one guard electrode associated with said sensing electrode;
    a first circuit coupled to said array to receive said electrocardiogram signal;
    a second circuit coupled to said array to generate a fringe capacitance signal based on any fringe capacitance between said at least one electrode and said at least one guard electrode;
    a compensation module programmed to actively gain correct said electrocardiogram signal based on said fringe capacitance signal by converting said fringe capacitance signal into a source capacitance value and dividing said electrocardiogram signal by said capacitance value and to adaptively filter said gain corrected signal using the least-mean square algorithm.

2. The sensor of claim 1, further comprising a third circuit coupled to said array to generate a static charge reference signal, wherein said compensation module is further programmed to filter said gain corrected signal based on said static charge reference signal.

3. The sensor of claim 1, wherein said first circuit includes a charge sensitive preamplifier.

4. The sensor of claim 3, wherein said charge sensitive preamplifier comprises a capacitive transducer, a composite amplifier coupled to the capacitive transducer, and a feedback capacitor coupled to the composite amplifier.

5. The sensor of claim 1, wherein said second circuit includes a capacitive sensing circuit.

6. The sensor of claim 5, wherein said third circuit includes a high impedance electrometer.

7. A method of obtaining electrocardiogram measurements, comprising the steps of:
    providing an electrode array comprising at least one sensing electrode for outputting an electrocardiogram signal and at least one guard electrode;
    receiving said electrocardiogram signal;
    generating a fringe capacitance signal based on a fringe capacitance between said at least one electrode and said at least one guard electrode;
    generating a static charge reference signal;
    actively gain correcting said electrocardiogram signal based on said fringe capacitance signal; and
    adaptively filtering said gain corrected signal based on said static charge reference signal using the least-mean square algorithm.

8. The method of claim 7, wherein the step of actively gain correcting said electrocardiogram signal based on said fringe capacitance signal comprises converting said fringe capacitance signal into a source capacitance value.

9. The method of claim 8, wherein said compensation module actively gain corrects said electrocardiogram signal by dividing said electrocardiogram signal by said source capacitance value.

10. The method of claim 7, wherein the step of receiving said electrocardiogram signal includes amplifying said electrocardiogram signal with a charge sensitive preamplifier.

11. The method of claim 10, wherein said charge sensitive preamplifier comprises a capacitive transducer, a composite amplifier coupled to the capacitive transducer, and a feedback capacitor coupled to the composite amplifier.

12. The method of claim 7, wherein said the step of generating a fringe capacitance signal based on a fringe capacitance between said at least one electrode and said at least one guard electrode comprises using a capacitive sensing circuit.

13. The method of claim 7, wherein the step of generating a static charge reference signal comprises using a high impedance electrometer.

14. The method of claim 7, wherein the step of actively gain correcting said electrocardiogram signal based on said fringe capacitance signal includes notch filtering said electrocardiogram signal.

* * * * *